United States Patent [19]

Shiba et al.

[11] Patent Number: 4,652,484

[45] Date of Patent: Mar. 24, 1987

[54] ABSORBENT ARTICLE

[75] Inventors: Daisuke Shiba; Iwao Miyashita; Osamu Ito, all of Utsunomiya, Japan

[73] Assignee: Kao Corporation, Tokyo, Japan

[21] Appl. No.: 756,523

[22] Filed: Jul. 18, 1985

[30] Foreign Application Priority Data

Jul. 25, 1984 [JP] Japan .................................. 59-154413

[51] Int. Cl.⁴ ............................................. B32B 27/00
[52] U.S. Cl. .................................... 428/286; 428/284; 428/287; 428/297; 428/298; 428/340; 428/373; 428/913; 604/372
[58] Field of Search ............... 428/373, 913, 284, 286, 428/287, 297, 298, 340; 604/370, 372

[56] References Cited

U.S. PATENT DOCUMENTS

| | | | |
|---|---|---|---|
| 4,381,611 | 5/1983 | Wishman | 428/284 |
| 4,424,258 | 1/1984 | Bach | 428/373 |
| 4,477,516 | 10/1984 | Sugihara et al. | 428/373 |
| 4,480,000 | 10/1984 | Watanabe et al. | 428/287 |

FOREIGN PATENT DOCUMENTS 0183139  9/1985  Japan .................................. 428/284

Primary Examiner—James J. Bell
Attorney, Agent, or Firm—Flynn, Thiel, Boutell & Tanis

[57] ABSTRACT

An absorbent article such as a sanitary napkin and a diaper is improved in the surface material by use of a non-woven fabric of hot-melt fibers which melts at 90° to 140° C. It is disposable.

4 Claims, No Drawings

ABSORBENT ARTICLE

The present invention relates to disposable absorbent articles, particularly, sanitary napkins and paper diapers. More particularly, the invention relates to disposable absorbent articles such as sanitary napkins and paper diapers having a surface made of a special, non-woven fabric.

Conventional absorbent articles such as paper diapers and sanitary napkins comprise an absorbent layer made of a cotton-like pulp or absorbent paper, a leakproof layer arranged below and around the absorbent layer and a non-woven fabric placed on the surface thereof.

The non-woven fabric forming the surface layer of the absorbent article should satisfy the following requirements: loosening of the absorbent is prevented, the flow of the liquid on the surface which invites leakage is controlled, the return of a body fluid kept in the absorbent layer toward the skin in minimized and a touch is improved.

Absorbing articles having a non-woven fabric satisfying these requirements are disclosed in the specifications of Japanese Patent Laid-Open Nos. 143750.1983 and 191356/1972.

The former articles are sanitary napkins characterized in that the surface material comprises 30 to 80 wt. % of hot-melt fibers and 70 to 20 wt. % of hydrophobic fibers. In these sanitary napkins having the surface made of the non-woven fabric, the blood penetrates rapidly into the napkin and is absorbed therein, the return of the blood due to a body weight of the user is minimized and a comfortable touch is obtained.

In the latter articles, the surface material is a non-woven fabric made of synthetic fibers having a relatively high fineness (6 denier or higher) and heat-bonded with hot-melt fibers to attain high compression elasticity and thickness. By using said non-woven fabric, the absorbent article which realizes a comfortable feeling upon use and in which the return is controlled can be obtained.

However, in the above-mentioned absorbent articles in which the non-woven fabric is used as the surface material, the non-woven fabric forming the surface layer is broken by vigorous motions of a user, such as a baby, and loss of non-hot melt fibers occurs causing marked deterioration in the shape retention of the absorbent layer, absorbing capacity and touch.

SUMMARY OF THE INVENTION

After intensive investigations made for the purpose of overcoming the defects of the non-woven fabrics used as the surface materials in the conventional absorbent articles, the inventors have found a surface material for the absorbent articles which protects the absorbent articles from breakage or loss of fibers due to pilling, which retains the shape of the absorbent layer and which maintains the absorbing capacity and comfortable touch even when the user moves vigorously. The present invention has been completed on the basis of this finding.

The present invention relates to an absorbent article having a surface material comprising a non-woven fabric made solely of hot-melt fibers and comprised at least partially of fibers which melt at 90° to 140° C.

Preferably, the non-woven fabric used in the present invention has a tensile strength of at least 250 g/25 mm and comprises the first layer forming the surface which is in contact with the skin of a user and the second layer which is not in contact with the skin, said first layer having a basis weight of 5 to 15 g/m², said second layer having a basis weight of 8 to 35 g/m², both layers comprising the first sterically non-buckled fibers of 1 to 3 denier and the second sterically buckled fibers of 1.5 to 6 denier, the weight ratio of said first fibers to said second fibers being 100 to 30/0 to 70 in said first layer and 50 to 0/50 to 100 in said second layer.

The breakage of the non-woven fabric used as the surface material and loss of fibers due to the vigorous motion of the user can be prevented even when the non-woven fabric is made of a mixture of said hot melt fibers and non-hot melt fibers by (1) increasing the quantity of heat applied in the heat-bonding of the web, (2) increasing the basis weight of the non-woven fabric or (3) reducing the relative amount (weight) of the non-hot melt fibers. However, these processes have defects. More particularly, according to the process (1) or (2), the feel to the user deteriorates, since the whole non-woven fabric becomes stiff and the roughness of the surface is increased. In addition, the increase of the basis weight increases the cost. The problem of loss of fibers of the non-hot melt fibers cannot be solved by the process (3).

When a non-woven fabric made of hot-melt fibers comprising at least partially fibers which melt at 90° to 140° C. is used as the surface material as in the present invention, a good touch can be realized and the breakage or loss of fibers can be minimized substantially without necessitating an increase of the basis weight.

For example, a strength sufficient for preventing the breakage during the use and a thickness sufficient for keeping the skin from contact with the body fluid retained in the absorbent layer are required of disposable diapers. Hot-melt fibers having a three-dimensional, sterically buckled structure are recommended for improving the strength, realizing a suitable thickness and controlling loss of fibers without increasing the basis weight while maintaining the comfortable touch.

The non-woven fabric of the present invention perferably has a strength of at least 250 g/25 mm so as to resist to the breakage due to the user's motion.

The larger the relative amount (weight) of the sterically, buckled, hot-melt fibers, the thicker the non-woven fabric but the poorer the touch. Therefore, the first layer forming the surface material of the non-woven fabric to be in contact with the skin comprises at least 30 wt. % of sterically non-buckled, hot-melt fibers. The fibers forming the first layer to be in contact with the skin are desirably as thin as about 1 to 3 denier from the viewpoint of feeling.

The second layer should contain at least 50% of sterically buckled, hot-melt fibers so as to have a desired thickness and the fibers have a thickness higher than that of the fibers in the first layer, i.e. 1.5 to 6 denier, preferably 3 to 6 denier.

The usable hot melt fibers are essentially those which are molten partially or wholly (preferably 30 to 70 wt. %) at a temperature of 90° to 140° C. to exhibit adhesive properties. Examples of the preferred fibers include polyethylene/polypropylene, low melting polyester/polyester, low melting polyester/polypropylene and polyethylene/polyester conjugate fibers.

The first layer has a basis weight of preferably at least about 5 g/m², since a comfortable hand is required because it is in contact with the skin. The basis weight should not exceed 15 g/m², since the layer having an excessive basis weight is stiff and has a poor feel upon use. The second layer is effective in mainly realizing the necessary thickness and strength. When the basis weight is less than 8 g/m², a sense of thickness is lost and the strength is lower than 250 g/25 mm. Though a high thickness can be obtained by increasing the basis weight of the second layer, an excessively high thickness causes a stiff feeling and is not preferred from the viewpoint of economy. Thus, the basis weight of the second layer is preferably 8 to 35 g/m².

The following examples will further illustrate the present invention.

EXAMPLES 1 TO 14 AND COMPARATIVE EXAMPLES 1 TO 4

Non-woven fabrics having compositions shown in Table 1 were used as the surface materials and the performances of them were examined by the following methods to obtain the results shown in Table 1.

(1) Tensile strength (CD direction): Test pieces having a width of 25 mm were torn at a pulling rate of 300 mm/min, the grab width being 150 mm. The tensile strength was shown in terms of the breaking strength. The direction of the tension was a CD direction of the non-woven fabric.
(2) Thickness: The thickness under a load of 1 g/cm² was measured.
(3) Feeling: The softness and the touch of the non-woven fabric were examined by organoleptic tests according to the following criteria:
   O: The sample was very soft and had a comfortable touch.
   Δ: The sample was soft but the touch was comparatively poor or, alternatively, the sample had an excellent touch but was comparatively stiff.
   X: The sample was stiff and had a poor touch.
(4) Loss of fibers: The surface of the non-woven fabric was rubbed with a sponge roll under a load of 15 g/cm² and the amount of the fibers which came off from the non-woven fabric and adhered to the sponge was examined. The results were shown according to the following criteria:
   O: Substantially no fibers were observed.
   Δ: The loss of fibers was remarkable but no pilling was observed.
   X: The loss of fibers and pilling were remarkable.

In the examples and comparative examples, fibers ES and ESHB were polyethylene/polypropylene conjugate fibers of Chisso Polypro Fibers Co., Ltd. ESHB was sterically bundled one. ESHB fibers were sterically buckled fibers. NBF fibers were sterically non-buckled polyethylene/polypropylene conjugate fibers of Daiwa Spinning Co., Ltd. "Melty" fibers were sterically non-buckled low melting polyester/polyester conjugate fibers of Unitika Ltd.

It is apparent from Table 1 that when the amount of the hot-melt fibers was 100 wt. %, the loss of fibers was scarcely observed, a sufficiently high tensile strength was obtained and that as the weight ratio of the sterically buckled fibers to said hot-melt fibers was increased, the thickness was increased. It is also suggested in Table 1 that, for maintaining the excellent feeling, the amount of the sterically non-buckled, hot-melt fibers in the first layer is desirably at least 30 wt. %.

TABLE 1

| | Basis weight | | Composition | | | | | | Tensile strength in CD direction | Thickness | | | |
| | 1st layer | 2nd layer | 1st layer | | | 2nd layer | | | | | | | |
| | | | fibers | fineness | ratio | fibers | fineness | ratio | g/25 mm | mm | Feeling | Pilling | Remarks |
| Example | | | | | | | | | | | | | |
| 1 | 10 | 25 | ES | 1.5 d | 60% | ES | 3 d | 30% | 412 | 1.4 | o | o | |
| | | | ESHB | 3 d | 40% | ESHB | 3 d | 70% | | | | | |
| 2 | " | " | ES | 3 | 60 | ES | 3 | 30 | 388 | 1.5 | o | o | |
| | | | ESHB | 3 | 40 | ESHB | 3 | 70 | | | | | |
| 3 | " | " | ES | 6 | 60 | ES | 3 | 30 | 368 | 1.5 | Δ | o | |
| | | | ESHB | 3 | 40 | ESHB | 3 | 70 | | | | | |
| 4 | " | " | ES | 18 | 60 | ES | 3 | 30 | 331 | 1.7 | Δ | o | |
| | | | ESHB | 3 | 40 | ESHB | 3 | 70 | | | | | |
| 5 | " | " | ES | 1.5 | 20 | ES | 3 | 30 | 384 | 1.9 | Δ | o | |
| | | | ESHB | 3 | 80 | ESHB | 3 | 70 | | | | | |
| 6 | " | " | ES | 1.5 | 40 | ES | 3 | 30 | 403 | 1.5 | o | o | |
| | | | ESHB | 3 | 60 | ESHB | 3 | 70 | | | | | |
| 7 | " | " | ES | 1.5 | 80 | ES | 3 | 30 | 435 | 1.3 | o | o | |
| | | | ESHB | 3 | 20 | ESHB | 3 | 70 | | | | | |
| 8 | " | " | ES | 3 d | 60% | ES | 3 d | 30% | 390 | 1.9 | o | o | |
| | | | ESHB | 3 d | 40% | ESHB | 6 d | 70% | | | | | |
| 9 | " | " | ES | 3 | 60 | ES | 3 | 30 | 333 | 2.3 | Δ | o | |
| | | | ESHB | 3 | 40 | ESHB | 18 | 70 | | | | | |
| 10 | " | " | ES | 3 | 60 | ES | 3 | 10 | 381 | 2.0 | o | o | |
| | | | ESHB | 3 | 40 | ESHB | 3 | 90 | | | | | |
| 11 | " | " | ES | 3 | 60 | ES | 3 | 60 | 410 | 1.1 | o | o | |
| | | | ESHB | 3 | 40 | ESHB | 3 | 40 | | | | | |
| 12 | " | " | ES | 3 | 60 | ES | 3 | 90 | 392 | 0.8 | o | o | |
| | | | ESHB | 3 | 40 | ESHB | 3 | 10 | | | | | |
| 13 | " | " | NBF | 3 | 60 | NBF | 3 | 30 | 420 | 1.4 | o | o | |
| | | | ESHB | 3 | 40 | ESHB | 3 | 70 | | | | | |
| 14 | " | " | Melty | 3 | 40 | Melty | 3 | 30 | 439 | 2.0 | o | o | |
| | | | ESHB | 3 | 60 | ESHB | 3 | 70 | | | | | |
| Comparative | | | | | | | | | | | | | |
| 1 | 30 | | Rayon | — | 50% | | | | — | 0.6 | o | x | Commercially avail- |
| | | | PET | — | 50% | | | | | | | | |

TABLE 1-continued

| | Basis weight | | Composition | | | | | | Tensile strength in CD direction g/25 mm | Thickness mm | Feeling | Pilling | Remarks |
| | 1st layer | 2nd layer | 1st layer | | | 2nd layer | | | | | | | |
| | | | fibers | fineness | ratio | fibers | fineness | ratio | | | | | |
|---|---|---|---|---|---|---|---|---|---|---|---|---|---|
| 2 | 100 | | PP | — | 100 | | | | — | 0.2 | o | Δ | Commercially available |
| 3 | 10 | 25 | ES | 3 | 100 | ES<br>PP | 3 d<br>6 d | 30%<br>70% | 203 | 1.2 | o | x | |
| 4 | 8 | 10 | ES | 1.5 | 100 | ES<br>PP | 3<br>6 | 30<br>70 | 87 | 0.4 | o | x | |

The embodiments of the invention in which an exclusive property or privilege is claimed are defined as follows:

1. In an absorbent article comprising an absorbent layer capable of absorbing a liquid, a leakproof layer on one side of said absorbent layer and a non-woven fabric layer on the opposite side of said absorbent layer, said non-woven fabric layer permitting penetration of liquid therethrough into said absorbent layer, the improvement which comprises: said non-woven fabric layer consists of hot-melt, adhesive, synthetic resin fibers consisting of (a) straight fibers of 1 to 3 denier, and (b) sterically buckled fibers of 1.5 to 6 denier, at least a portion of said synthetic resin fibers having a melting point in the range of from 90° to 140° C., said non-woven fabric layer having a tensile strength of at least 250 g/25 mm, said non-woven fabric layer consisting essentially of an assembly of a first sublayer having a basis weight of 5 to 15 g/m² and a second sublayer having a basis weight of 8 to 35 g/m², said first sublayer being located remote from said absorbent layer and being adapted to contact the skin of a user, said second layer being adjacent to said absorbent layer, the weight ratio of fibers (a)/fibers (b) being 100–30/0–70 in said first sublayer and being 50–0/50–100 in said second sublayer.

2. An absorbent article as claimed in claim 1 in which from 30 to 70% of said hot-melt synthetic resin fibers melt at 90° to 140° C.

3. An absorbent article as claimed in claim 1 in which all of the fibers in said first sublayer are fibers of 1 to 3 denier and said fibers (b) in said second sublayer are fibers of 3 to 6 denier.

4. An absorbent article as claimed in claim 1 in which said synthetic resin fibers are selected from the group consisting of polyethylene/polypropylene conjugate fibers, low melting polyester/polyester conjugate fibers, low melting polyester/polypropylene conjugate fibers and polyethylene/polyester conjugate fibers.

* * * * *